(12) United States Patent
Satou

(10) Patent No.: US 8,519,065 B2
(45) Date of Patent: Aug. 27, 2013

(54) EPOXY COMPOUND, CURABLE COMPOSITION, AND CURED PRODUCT THEREOF

(75) Inventor: Yutaka Satou, Ichihara (JP)

(73) Assignee: DIC Corporation, Tokyo (JP)

( * ) Notice: Subject to any disclaimer, the term of this patent is extended or adjusted under 35 U.S.C. 154(b) by 0 days.

(21) Appl. No.: 13/816,084

(22) PCT Filed: Aug. 3, 2011

(86) PCT No.: PCT/JP2011/067771
§ 371 (c)(1),
(2), (4) Date: Feb. 8, 2013

(87) PCT Pub. No.: WO2012/023435
PCT Pub. Date: Feb. 23, 2012

(65) Prior Publication Data
US 2013/0144030 A1   Jun. 6, 2013

(30) Foreign Application Priority Data
Aug. 19, 2010 (JP) ................................. 2010-183901

(51) Int. Cl.
*C08G 59/08* (2006.01)
*C08L 63/04* (2006.01)

(52) U.S. Cl.
USPC ........... 525/481; 525/423; 525/510; 525/523; 525/524; 525/533; 528/97

(58) Field of Classification Search
None
See application file for complete search history.

(56) References Cited

U.S. PATENT DOCUMENTS
4,551,508 A    11/1985  Urasaki

FOREIGN PATENT DOCUMENTS

| | | | |
|---|---|---|---|
| JP | 59-230017 A | | 12/1984 |
| JP | 62-20206 B2 | | 12/1984 |
| JP | 4-323214 A | * | 11/1992 |
| JP | 04-323214 A | | 11/1992 |
| JP | 5-287052 A | * | 11/1993 |
| JP | 05-287052 A | | 11/1993 |
| JP | 09-291127 A | | 11/1997 |
| JP | 9-291127 A | * | 11/1997 |
| JP | 2000-038430 A | | 2/2000 |
| JP | 2003-306470 A | * | 10/2003 |
| JP | 2004-277624 A | | 10/2004 |
| JP | 2009-185174 A | * | 8/2009 |

OTHER PUBLICATIONS
International Search Report dated Nov. 1, 2011, issued for PCT/JP2011/067771.

* cited by examiner

*Primary Examiner* — Robert Sellers
(74) *Attorney, Agent, or Firm* — Edwards Wildman Palmer LLP

(57) ABSTRACT

A problem to be solved by the invention is to provide a novel epoxy resin exhibiting excellent performance with respect to heat resistance and low thermal expansibility of a cured product, a curable composition using the same, and a cured product having excellent heat resistance and low thermal expansibility. The curable composition contains an epoxy compound and a curing agent as essential components, a calixarene-type novel epoxy compound being used as the epoxy compound. The novel epoxy compound has a resin structure represented by structural formula 1 below (in the formula, $R^1$s each independently represent a hydrogen atom, an alkyl group, or an alkoxy group, and n is a repeat unit and an integer of 2 to 10).

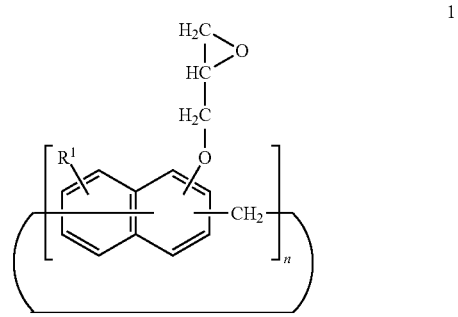

7 Claims, 3 Drawing Sheets

EPOXY COMPOUND, CURABLE COMPOSITION, AND CURED PRODUCT THEREOF

TECHNICAL FIELD

The present invention relates to an epoxy compound which produces a cured product having excellent heat resistance and low thermal expansibility and which can be preferably used for applications such as a printed circuit board, a semiconductor encapsulant, a coating material, cast molding, etc., a curable composition containing the epoxy compound, and a cured product thereof.

BACKGROUND ART

Epoxy resins are used for adhesives, molding materials, coating materials, photoresist materials, color developing materials, etc., and in view of the excellent heat resistance and moisture resistance of resultant cured products, epoxy resins are widely used in the electric and electronic field such as a semiconductor encapsulant, an insulating material for a printed circuit board, etc.

Among these various applications, in the field of printed circuit boards, the tendency toward higher densities due to narrowing of the wiring pitches of semiconductor devices becomes remarked with miniaturization and improvement in performance of electronic apparatuses. As a semiconductor mounting method corresponding to this, a flip-chip bonding method of bonding a semiconductor device and a substrate with solder balls is widely used. The flip-chip bonding method is a so-called reflow-system semiconductor mounting method in which solder balls are disposed between a circuit board and a semiconductor and the whole is heated to cause fused-junction between the circuit board and the semiconductor. Therefore, the circuit board is exposed to a high-heat environment during solder reflowing, and thus large stress occurs in the solder balls, which are used for bonding together the circuit board and the semiconductor, due to thermal contraction of the circuit board, thereby causing faulty connection in wiring. Therefore, a low-thermal-expansion material is required as an insulating material used for printed circuit boards.

In addition, high-melting-point solder not using lead has become a main stream by the legal regulations for environmental problems. The lead-free solder is used at a temperature about 20 to 40° C. higher than that for usual eutectic solder, and thus a curable resin composition is required to have higher heat resistance.

Printed circuit boards are generally manufactured by curing and molding curable resin compositions, each of which contains an epoxy resin as a main component, integral with glass woven fabrics, and improvements in epoxy resins are required for achieving higher heat resistance and lower thermal expansibility.

In order to comply with these requirements, for example, a naphthalene-type epoxy resin produced by condensation of a naphthol compound with formaldehyde and then reaction with epichlorohydrin is known as a material capable of resolving the technical problems of heat resistance etc. (refer to Patent Literature 1 below).

CITATION LIST

Patent Literature

PTL 1: Japanese Examined Patent Application Publication No. 62-20206

SUMMARY OF INVENTION

Technical Problem

However, the naphthol novolac epoxy resin described in Patent Literature 1 is found to have the effect of improving heat resistance of epoxy resin cured products due to rigidity of its skeleton as compared with general phenol novolac epoxy resins. However, the heat resistance improving effect does not reach a level sufficiently satisfying the present required level. Further, the naphthol novolac epoxy resin has a certain effect of decreasing thermal expansion due to the orientation of the naphthalene skeleton, but the effect does not each a satisfactory level.

Accordingly, a problem to be solved by the invention is to provide a novel epoxy compound which exhibits excellent performance with respect to heat resistance and low thermal expansibility of a cured product, a curable composition containing the epoxy resin, and a cured product having excellent heat resistance and low thermal expansibility.

Solution to Problem

As a result of intensive research for resolving the problem, the inventors have found that when an epoxy compound produced by epoxidizing a calixarene-type naphthol compound, which is produced by reaction of α-naphthol with formaldehyde under predetermined conditions, is used as a main component of a heat-curable resin, a cured product thereof exhibits excellent heat resistance and low linear expansibility, leading to the achievement of the present invention.

The present invention relates to a novel epoxy compound having a resin structure represented by structural formula 1 below.

[Chem. 1]

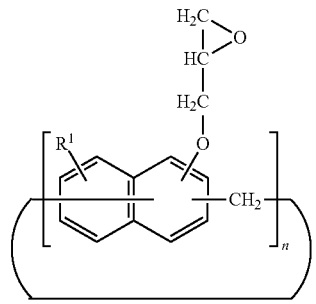

(In the formula, $R^1$s each independently represent a hydrogen atom, an alkyl group, or an alkoxy group, and n is a repeat unit and an integer of 2 to 10.)

The present invention further relates to a curable resin composition containing an epoxy compound (A) and a curing agent (B) as essential components, the above-described novel epoxy compound being used as the epoxy compound (A).

The present invention further relates to a cured product produced by a curing reaction of the curable resin composition.

Advantageous Effects of Invention

According to the present invention, it is possible to provide a novel epoxy compound exhibiting excellent performance with respect to heat resistance and low thermal expansibility of a cured product, a curable composition using the epoxy compound, and a cured product having excellent heat resistance and low thermal expansibility.

DESCRIPTION OF EMBODIMENTS

Figure 1:
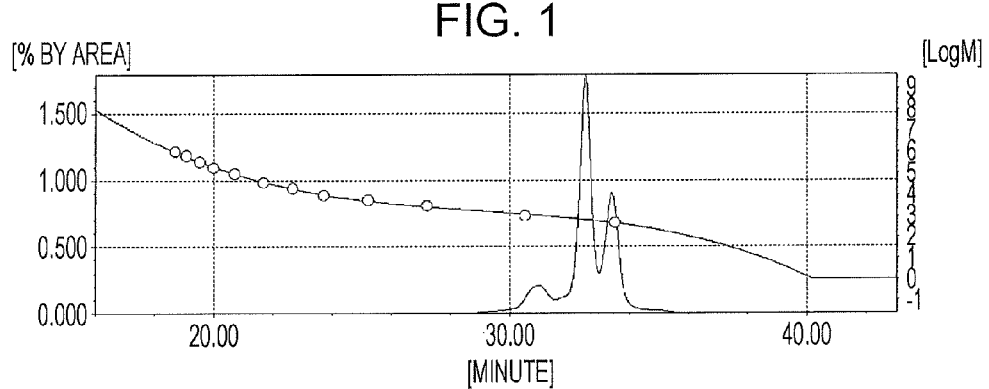
FIG. 1 is a GPC chart of naphthol compound (A-1) produced in Example 1.

The present invention is described in detail below.
As described above, a novel epoxy compound, of the present invention has a resin structure represented by structural formula 1 below.

[Chem. 2]

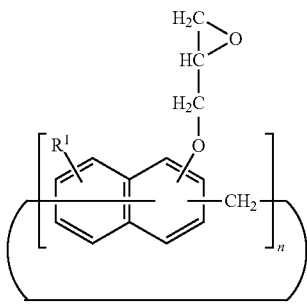

(In the formula, $R^1$s each independently represent a hydrogen atom, an alkyl group, or an alkoxy group, and n is a repeat unit and an integer of 2 to 10.)

The novel epoxy compound of the present invention has a so-called calixarene-type cyclic structure and thus a cured product of the epoxy compound is suppressed from molecular movement, resulting in expression of excellent heat resistance. In the structural formula 1, bond positions of methylene groups on a naphthalene ring are desired sites, preferably two bond sites on the same ring in view of easy production of the novel epoxy compound, and particularly a methylene group is preferably bonded at the 2- and 4-positions of the naphthalene ring in view of excellent heat resistance and low linear expansibility of a cured product due to the formation of a regular molecular structure.

In addition, in the structural formula 1, n is an integer of 2 to 10, but is preferably 2, 4, 6, or 8 and most preferably 4 in view of excellent symmetry of the chemical structure and the significant effect of improving heat resistance.

The structure of the novel epoxy compound can be identified by confirming the molecular weight of a theoretical structure based on a MS spectrum.

As described above, $R^1$ in the structural formula 1 represents a hydrogen atom, an alkyl group, or an alkoxy group. Examples of the alkyl group include alkyl groups having 1 to 4 carbon atoms, such as a methyl group, an ethyl group, an isopropyl group, a tert-butyl group, and the like, and examples of the alkoxy group include alkoxy groups having 1 to 4 carbon atoms, such as a methoxy group, an ethoxy group, an isopropyloxy group, a tert-butyloxy group, and the like. In the present invention; $R^1$ is preferably a hydrogen atom, a methyl group, an ethyl group, or a methoxy group, and particularly preferably a hydrogen atom in view of the excellent heat resistance of a cured product.

Although a naphthol skeleton in the structural formula 1 may be either an α-naphthol skeleton or a β-naphthol skeleton, in the present invention, an α-naphthol skeleton is preferred from the viewpoint of excellent heat resistance and low thermal expansibility of a finally produced epoxy resin cured product. Further, in the present invention, an α-naphthol skeleton and a β-naphthol skeleton may coexist as the naphthol skeleton. In this case, with respect to the ratio between both skeletons present, the ratio of a β-naphthol compound is preferably 1.2 moles or less per mole of an α-naphthol compound in view of the low thermal expansibility.

The novel epoxy compound of the present invention can be produced by a method described below.

That is, the epoxy compound can be produced by a method in which a naphthol compound is reacted with formaldehyde at a molar ratio (naphthol compound/formaldehyde) of 1.0/1.0 to 1.0/2.0 in the presence of a basic catalyst to produce a calixarene-type naphthol compound (step 1), which is then epoxidized by reaction with epihalohydrin in the presence of a basic catalyst (step 2).

Specifically, the reaction in the step 1 can be performed at a temperature condition of 20° C. to 100° C.

Specifically, the naphthol compound used in the step 1 is α-naphthol, β-naphthol, a compound in which an aromatic nucleus of α-naphthol or β-naphthol is substituted with an alkyl group having 1 to 4 carbon atoms, such as a methyl group, an ethyl group, an isopropyl group, a tert-butyl group, or the like, or a compound in which an aromatic nucleus of α-naphthol or β-naphthol is substituted with an alkoxy group having 1 to 4 carbon atoms, such as a methoxy group, an ethoxy group, an isopropyloxy group, a tert-butyloxy group, or the like. Specific examples thereof include α-naphthol compounds, such as α-naphthol, 1-hydroxy-3-methylnaphthalene, 1-hydroxy-5-methylnaphthalene, 1-hydroxy-6-methylnaphthalene, 1-hydroxy-5-ethylnaphthalene, 1-hydroxy-6-ethylnaphthalene, 1-hydroxy-5-butylnaphthalene, 1-hydroxy-6-butylnaphthalene, 1-hydroxy-5-propylnaphthalene, 1-hydroxy-6-propylnaphthalene, 1-hydroxy-5-methoxynaphthalene, 1-hydroxy-6-methoxynaphthalene, 1-hydroxy-5-ethoxynaphthalene, 1-hydroxy-6-ethoxynaphthalene, 1-hydroxy-5-propyloxynaphthalene, 1-hydroxy-6-propyloxynaphthalene, 1-hydroxy-5-butyloxynaphthalene, 1-hydroxy-6-butyloxynaphthalene, and the like; β-naphthol compounds, such as β-naphthol, 2-hydroxy-3-methylnaphthalene, 2-hydroxy-5-methylnaphthalene, 2-hydroxy-6-methylnaphthalene, 2-hydroxy-5-ethylnaphthalene, 2-hydroxy-6-ethylnaphthalene, 2-hydroxy-5-butylnaphthalene, 2-hydroxy-6-butylnaphthalene, 2-hydroxy-5-propylnaphthalene, 2-hydroxy-6-propylnaphthalene, 2-hydroxy-5-methoxynaphthalene, 2-hydroxy-6-methoxynaphthalene, 2-hydroxy-5-ethoxynaphthalene, 2-hydroxy-6-ethoxynaphthalene, 2-hydroxy-5-propyloxynaphthalene, 2-hydroxy-6- propyloxynaphthalene, 2-hydroxy-5-butyloxynaphthalene, 2-hydroxy-6-butyloxynaphthalene, and the like. However, the α-naphthol compounds, particularly α-naphthol, is preferred in view of low thermal expansibility of the finally produced epoxy resin cured product.

In addition, in the present invention, the α-naphthol compound and the β-naphthol compound may be used in combination. In this case, the ratio of the β-naphthol compound is preferably 1.2 moles or less per mole of the α-naphthol compound in view of the low thermal expansibility.

On the other hand, examples of a formaldehyde source used in the step 1 include formalin, para-formaldehyde, trioxane, and the like. The formalin is preferably 30 to 60 mass % formalin in view of water reducibility and production workability.

Examples of the basic catalyst used in the step 1 include alkaline-earth metal hydroxides, alkali metal carbonates, alkali metal hydroxides, and the like. In particular, alkali metal hydroxides such as sodium hydroxide, potassium hydroxide, and the like are preferred in view of excellent catalytic activity. When the basic catalyst is used, it may be used in the form of an aqueous solution of about 10 to 55% by mass or in a solid form.

In addition, the amount of the basic catalyst used in the step 1 is preferably 0.02 moles or more per mole of the naphthol compound in view of easy formation of a calixarene structure. Further, the molar ratio (naphthol compound/formaldehyde) is preferably 1.0 or less from the viewpoint that selectivity for a naphthol-type calix(4)arene compound which is the most preferred molecular structure can be enhanced. The naphthol-type calix(4)arene compound is a compound in which 4 molecules of α-naphthol compound are bonded to each other through methylene bonds to form a cyclic structure.

In the next step 2, the intended epoxy compound can be produced by reaction of the calixarene-type naphthol compound produced in the step 1 with epihalohydrin.

Specifically, the step 2 can be performed by a method including adding epihalohydrin in an amount of 2 to 10 times (molar basis) the number of moles of phenolic hydroxyl groups in the calixarene-type naphthol compound, and reacting these compounds at a temperature of 20° C. to 120° C. for 0.5 to 10 hours while further adding collectively or gradually the basic catalyst in an amount of 0.9 to 2.0 times (molar basis) the number of moles of phenolic hydroxyl groups. The basic catalyst may be used as a solid or an aqueous solution. When an aqueous solution is used, the method may be one in which the basic catalyst is continuously added and water and epihalohydrins are continuously distilled off from the reaction mixture under reduced pressure or normal pressure and further fractionated so that water is removed, and epihalohydrin is continuously returned to the reaction mixture.

In the case of industrial production, new epihalohydrin to be charged is used in a first batch for production of the epoxy compound, but in subsequent batches, the epihalohydrin recovered from the crude reaction product is preferably combined with new epihalohydrin corresponding to a consumption loss by the reaction. In this case, the epihalohydrin used is not particularly limited but, for example, epichlorohydrin, epibromohydrin, β-methylepichlorohydrin, or the like can be used. In particular, epichlorohydrin is preferred because of easily industrial availability.

Like in the step 1, examples of the basic catalyst include alkaline-earth metal hydroxides, alkali metal carbonates, alkali metal hydroxides, and the like. In particular, in view of excellent catalytic activity for epoxidation reaction, alkali metal hydroxides such as sodium hydroxide, potassium hydroxide, and the like are preferred. When the basic catalyst is used, it may be used in the form of an about 10 to 55 mass % aqueous solution or a solid form. In addition, combination with an organic solvent can increase the reaction rate of synthesis of the epoxy compound. Examples of the organic solvent include, but are not particularly limited to, ketones such as acetone, methyl ethyl ketone, and the like; alcohols such as methanol, ethanol, 1-propyl alcohol, isopropyl alcohol, 1-butanol, secondary butanol, tertiary butanol, and the like; cellosolves such as methyl cellosolve, ethyl cellosolve, and the like; ethers such as tetrahydrofuran, 1,4-dioxane, 1,3-dioxane, diethoxyethane, and the like; and aprotic polar solvents such as acetonitrile, dimethylsulfoxide, dimethylformamide, and the like. These organic solvents may be used alone or in combination of two or more in order to adjust polarity.

The product of the epoxidation reaction is washed with water and then unreacted epihalohydrin and the organic solvent used are distilled off by distillation under heating and reduced pressure. Further, in order to produce the epoxy compound containing little hydrolyzable halogen, the resultant epoxy compound can be again dissolved in an organic solvent such as toluene, methyl isobutyl ketone, methyl ethyl ketone, or the like, and an aqueous solution of an alkali metal hydroxide such as sodium hydroxide, potassium hydroxide, or the like can be added to effect further reaction. In this case, a phase transfer catalyst, such as a quaternary ammonium salt, a crown ether, or the like, may be present for improving the reaction rate. When the phase transfer catalyst is used, the amount of use thereof is preferably in a range of 0.1 to 3.0 parts by mass relative to 100 parts by mass of the epoxy resin used. After the completion of reaction, the produced salt can be removed by filtration and water-washing, and the solvent such as toluene or methyl isobutyl ketone can be distilled off by heating under reduced pressure to produce the intended epoxy compound.

A curable composition of the present invention uses the above-detailed novel epoxy compound as an epoxy compound (A) used as a main component. In this case, as a curing agent (B) used in the curable composition, various known curing agents, for example, an amine compound, an amide compound, an acid anhydride compound, a phenol compound, and the like, can be used. Examples of the amine compound include diaminodiphenylmethane, diethylene triamine, triethylene tetramine, diaminodiphenylsulfone, isophorone diamine, imidazole, $BF_3$-amine complex, guanidine derivatives, and the like. Examples of the amide compound include dicyandiamide, polyamide resins synthesized from linolenic acid dimer and ethylenediamine, and the like. Examples of the acid anhydride compound include phthalic anhydride, trimellitic anhydride, pyromellitic anhydride, maleic anhydride, tetrahydrophthalic anhydride, methyltetrahydrophthalic anhydride, methylnadic anhydride, hexahydrophthalic anhydride, methylhexahydrophthalic anhydride, and the like. Examples of the phenol compound include polyhydric phenol compounds, such as phenol novolac resins, cresol novolac resins, aromatic hydrocarbon formaldehyde resin-modified phenol resins, dicyclopentadiene phenol addition-type resins, phenol aralkyl resins (xylok resins), naphthol aralkyl resins, trimethylolmethane resins, tetraphenylolethane resins, naphthol novolac resins, naphthol-phenol co-condensed novolac resins, naphthol-cresol co-condensed novolac resins, biphenyl-modified phenol resins (polyhydric phenol compounds including phenol nuclei connected through a bismethylene group), biphenyl-modified naphthol resins (polyhydric naphthol compounds including phenol nuclei connected through a bismethylene group), aminotriazine-modified phenol resins (polyhydric phenol compounds including phenol nuclei connected through melamine or benzoguanamine), alkoxy group-containing aromatic ring modified novolac resins (polyhydric phenol compounds including a phenol nucleus and an alkoxy group-containing aromatic ring which are connected through formaldehyde), and the like.

The mixing ratio between the epoxy compound (A) and the curing agent (B) which are detailed above is preferably such that the equivalent ratio (epoxy group/active hydrogen atom) of epoxy group in the epoxy compound (A) to active hydrogen atom in the curing agent (B) is 1/0.5 to 1/1.5 in view of excellent heat resistance.

The curable composition of the present invention preferably further contains, in addition to the epoxy, compound (A) and the curing agent (B), a naphthalene-based epoxy resin (A') (hereinafter abbreviated as a "naphthalene-based epoxy resin (A')") other than the epoxy compound (A) in view of easy preparation of a composition for a printed circuit board due to improvement in solvent solubility of the composition.

Examples of the naphthalene-based epoxy resin (A') used include 2,7-diglycidyloxynaphthalene, α-naphthol novolac epoxy resins, β-naphthol novolac epoxy resins, α-naphthol/β-naphthol co-condensed novolac polyglycidyl ether, naphthol aralkyl epoxy resins, 1,1-bis(2,7-diglycidyloxy-1-naphthyl)alkanes, and the like. Among these, 2,7-diglycidyloxynaphthalene, α-naphthol novolac epoxy resins, β-naphthol novolac epoxy resins, and α-naphthol/β-naphthol co-condensed novolac polyglycidyl ether are particularly preferred in view of excellent compatibility with the epoxy compound (A). In particular, in the present invention, when a calixarene-type naphthol compound as a precursor of the epoxy resin (A) is produced, it is preferred from the viewpoint of excellent solvent solubility that α-naphthol and β-naphthol are used in combination to prepare a mixture of the calixarene-type naphthol compound and α-naphthol/β-naphthol co-condensed novolac, and then the mixture is epoxidized to produce a mixture of the epoxy compound (A) and α-naphthol/β-naphthol co-condensed novolac polyglycidyl ether.

The ratio between the epoxy compound (A) and the naphthalene-based epoxy resin (A') present is preferably such that in view of excellent heat resistance and solvent solubility of a cured product, the ratio of the naphthalene-based epoxy resin (A') is 3 to 50% in terms of area ratio in GPC measurement of a mixture of both.

In the curable composition of the present invention, in addition to the naphthalene-based epoxy resin (A'), another epoxy resin (A") may be used as an epoxy compound or epoxy resin component which can be used in combination with the epoxy compound (A) within a range where solubility of the resin components in an organic solvent is not impaired. The amount of the other epoxy resin (A") used is preferably in a range of, for example, 5 to 50% by mass in the total epoxy component.

As the other epoxy resin (A"), various epoxy resins can be used. Examples thereof include bisphenol epoxy resins such as bisphenol A epoxy resins, bisphenol F epoxy resins, and the like; biphenyl epoxy resins such as biphenyl epoxy resins, tetramethylbiphenyl epoxy resins, and the like; novolac epoxy resins such as phenol novolac epoxy resins, cresol novolac epoxy resins, bisphenol A novolac epoxy resins, epoxy compounds of condensates of phenol compounds and phenolic hydroxyl group-containing aromatic aldehydes, biphenyl novolac epoxy resins, and the like; triphenylmethane-type epoxy resins; tetraphenylethane-type epoxy resins; dicyclopentadiene-phenol addition reaction-type epoxy resins; phenol aralkyl-type epoxy resins; phosphorus atom-containing epoxy resins; and the like. These epoxy resins may be used alone or used as a mixture of two or more.

The phosphorus atom-containing epoxy resins include epoxy compound of 9,10-dihydro-9-oxa-10-phosphaphenanthrene-10-oxide (hereinafter abbreviated as "HCA"), epoxy compounds of phenol resins produced by reaction between HCA and quinones, HCA-modified phenol novolac epoxy resins, HCA-modified cresol novolac epoxy resins, bisphenol A epoxy resins modified with phenol resins which are produced by reaction between HCA and quinones, and the like.

When the naphthalene-based epoxy resin (A') and the other epoxy resin (A") are further used, the ratio of the curing agent (B) mixed is preferably such that the equivalent ratio (epoxy group/active hydrogen atom) of epoxy groups in all epoxy components in the curable composition to active hydrogen atoms in the curing agent (B) is 1/0.5 to 1/1.5 in view of good curability and excellent heat resistance of a cured product.

If required, the curable composition of the present invention may be properly combined with a curing accelerator. As the curing accelerator, various compounds can be used, and for example, a phosphorus-based compound, a tertiary amine, imidazole, an organic acid metal salt, a Lewis acid, an amine complex salt, and the like can be used. In particular, in application to a semiconductor encapsulating material, from the viewpoint of excellent curability, heat resistance, electric characteristics, moisture-resistance reliability, etc, 2-ethyl-4-methylimidazole is preferred as the imidazole compound, triphenylphosphine is preferred as the phosphorus-based compound, and 1,8-diazabicyclo-[5.4.0]-undecene (DBU) is preferred as the tertiary amine.

When the above-detained curable composition of the present invention is prepared into a varnish for a printed circuit board, the above-described components are preferably mixed with another organic solvent (C). Examples of the organic solvent which can be used include methyl ethyl ketone, acetone, dimethylformamide, methyl isobutyl ketone, methoxypropanol, cyclohexanone, methyl cellosolve, ethyl diglycol acetate, propyleneglycol monomethyl ether acetate, and the like. The type and proper amount of use can be appropriately selected according to applications, but for example, in application to a printed circuit board, a polar solvent having a boiling point of 160° C. or less, such as methyl ethyl ketone, acetone, dimethylformamide, or the like, is preferably used at a nonvolatile component ratio of 40 to 80% by mass. On the other hand, in application to an adhesive film for build-up, preferred examples of the organic solvent include ketones such as acetone, methyl ethyl ketone, cyclohexanone, and the like; acetic acid esters such as ethyl acetate, butyl acetate, cellosolve acetate, propylene glycol monomethyl ether acetate, carbitol acetate, and the like; carbitols such as cellosolve, butyl carbitol, and the like; aromatic hydrocarbons such as toluene, xylene, and the like; dimethylformamide; dimethylacetamide; N-methylpyrrolidone; and the like. In addition, such an organic solvent is preferably used at a nonvolatile content ratio of 30 to 60% by mass.

For example, in the field of printed circuit boards, in order to further enhance flame retardancy, the curable composition may be further mixed with a non-halogen flame retardant substantially not containing halogen atom.

Examples of the non-halogen flame retardant include a phosphorus-based flame retardant, a nitrogen-based flame retardant, a silicone-based flame retardant, an inorganic flame retardant, an organic metal salt-based flame retardant, and the like. Use of these flame retardants is not particularly limited, and they may be used alone or in combination of a plurality of flame retardants of the same type or different types.

As the phosphorus-based flame retardant, either an inorganic type or an organic type can be used. Examples of an inorganic compound include red phosphorus; ammonium phosphates such as monoammonium phosphate, diammonium phosphate, triammonium phosphate, ammonium polyphosphate, and the like; and inorganic nitrogen-containing phosphorus compounds such as phosphoric amide, and the like.

The red phosphorus is preferably surface-treated for preventing hydrolysis or the like. Examples of a surface treatment method include (i) a method of coating with an inorganic compound such as magnesium hydroxide, aluminum hydroxide, zinc hydroxide, titanium hydroxide, bismuth oxide, bismuth hydroxide, bismuth nitrate, or a mixture thereof, (ii) a method of coating with a mixture of an inorganic compound, such as magnesium hydroxide, aluminum hydroxide, zinc hydroxide, or titanium hydroxide, and a thermosetting resin, such as a phenol resin, (iii) a doubly coating method of coating with a film of an inorganic compound such as magnesium hydroxide, aluminum hydroxide, zinc hydroxide, or titanium hydroxide, and coating the film with a thermosetting resin such as a phenol resin, and the like.

Examples of the organic phosphorus compound include general-purpose organic phosphorus compounds such as phosphate compounds, phosphonic acid compounds, phosphinic acid compounds, phosphine oxide compounds, phospholan compounds, organic nitrogen-containing phosphorus compounds, and the like; cyclic organic phosphorus compounds such as 9,10-dihydro-9-oxa-10-phosphaphenanthrene=10-oxide, 10-(2,5-dihydroxyphenyl)-10H-9-oxa-10-phosphaphenanthrene=10-oxide, 10-(2,7-dihydroxynaphthyl)-10H-9-oxa-10-phosphaphenanthrene=10-oxide, and the like; and derivatives produced by reaction of these cyclic organic phosphorus compounds with a compound such as an epoxy resin, a phenol resin, or the like.

The mixing amount is appropriately selected according to the type of the phosphorus-based flame retardant, the other components of the curable resin composition, and the desired degree of flame retardancy. For example, when red phosphorus is used as the non-halogen flame retardant, the flame retardant is preferably mixed in a rage of 0.1 to 2.0 parts by mass in 100 parts by mass of the curable composition containing all of the epoxy component, the curing agent, filler, and the other additives. Similarly, when the organic phosphorus compound is used, it is preferably mixed in a range of 0.1 to 10.0 parts by mass, particularly preferably in a range of 0.5 to 6.0 parts by mass.

When the phosphorus-based flame retardant is used, the phosphorus-based flame retardant may be combined with hydrotalcite, magnesium hydroxide, a boron compound, zirconium oxide, a black dye, calcium carbonate, zeolite, zinc molybdate, activated carbon, or the like.

Examples of the nitrogen-based flame retardant include triazine compounds, cyanuric acid compounds, isocyanuric acid compounds, phenothiazine, and the like, and the triazine compounds, the cyanuric acid compounds, and the isocyanuric acid compounds are preferred.

Examples of the triazine compounds include melamine, acetoguanamine, benzoguanamine, melon, melam, succinoguanamine, ethylenedimelamine, melamine polyphosphate, triguanamine, and other compounds such as (i) aminotriazine sulfate compounds such as guanylmelamine sulfate, melem sulfate, melam sulfate, and the like; (ii) co-condensates of phenol compounds, such as phenol, cresol, xylenol, butylphenol, and nonylphenol, with melamines, such as melamine, benzoguanamine, acetoguanamine, and formguanamine, and formaldehyde; (iii) mixtures of the co-condensates (ii) and phenol resins such as phenol-formaldehyde condensates; and (iv) modifications of the co-condensates (ii) and the mixtures (iii) further modified with tung oil, isomerized linseed oil, or the like.

Examples of the cyanuric acid compounds include cyanuric acid, melamine cyanurate, and the like.

The amount of the nitrogen-based flame retardant mixed is appropriately selected according to the type of the nitrogen-based flame retardant, the other components of the curable resin composition, and the desired degree of flame retardancy. For example, the nitrogen-based flame retardant is preferably mixed in a range of 0.05 to 10 parts by mass, particularly preferably in a range of 0.1 to 5 parts by mass, in 100 parts by mass of the curable resin composition containing all of the epoxy component, the curing agent, the non-halogen flame retardant, filler, and the other additives.

In addition, the nitrogen-based flame retardant may be used in combination with a metal hydroxide, a molybdenum compound, or the like.

The silicone-based flame retardant is not particularly limited and can be used as long as it is an organic compound containing a silicon atom. Examples thereof include silicone oil, silicone rubber, silicone resins, and the like.

The amount of the silicone-based flame retardant mixed is appropriately selected according to the type of the silicone-based flame retardant, the other components of the curable resin composition, and the desired degree of flame retardancy. For example, the silicone-based flame retardant is preferably mixed in a range of 0.05 to 20 parts by mass in 100 parts by mass of the curable resin composition containing all of the epoxy component, the curing agent, the non-halogen flame retardant, filler, and the other additives. In addition, the silicone-based flame retardant may be used in combination with a molybdenum compound, alumina, or the like.

Examples of the inorganic flame retardant include metal hydroxides, metal oxides, metal carbonate compounds, metal powders, boron compounds, low-melting-point glass, and the like.

Examples of the metal hydroxides include aluminum hydroxide, magnesium hydroxide, dolomite, hydrotalcite, calcium hydroxide, barium hydroxide, zirconium hydroxide, and the like.

Examples of the metal oxides include zinc molybdate, molybdenum trioxide, zinc stannate, tin oxide, aluminum oxide, iron oxide, titanium oxide, manganese oxide, zirconium oxide, zinc oxide, molybdenum oxide, cobalt oxide, bismuth oxide, chromium oxide, nickel oxide, copper oxide, tungsten oxide, and the like.

Examples of the metal carbonate compounds include zinc carbonate, magnesium carbonate, calcium carbonate, barium carbonate, basic magnesium carbonate, aluminum carbonate, iron carbonate, cobalt carbonate, titanium carbonate, and the like.

Examples of the metal powders include powders of aluminum, iron, titanium, manganese, zinc, molybdenum, cobalt, bismuth, chromium, nickel, copper, tungsten, tin, and the like.

Examples of the boron compounds include zinc borate, zinc metaborate, barium metaborate, boric acid, borax, and the like.

Examples of the low-melting-point glass include Seaplea (Bokusui Brown Co., Ltd.), hydrated glass $SiO_2$—$MgO$—$H_2O$, and $PbO$—$B_2O_3$-based, $ZnO$—$P_2O_5$—$MgO$-based, $P_2O_5$—$B_2O_3$—$PbO$—$MgO$-based, $P$—$Sn$—$O$—$F$-based, $PbO$—$V_2O_5$—$TeO_2$-based, $Al_2O_3$—$H_2O$-based, and lead borosilicate-based glass compounds.

The amount of the inorganic flame retardant mixed is appropriately selected according to the type of the inorganic flame retardant, the other components of the curable resin composition, and the desired degree of flame retardancy. For example, the inorganic flame retardant is preferably mixed in a range of 0.5 to 50 parts by mass, particularly preferably in a range of 5 to 30 parts by mass, in 100 parts by mass of the curable resin composition containing all of the epoxy component, the curing agent, the non-halogen flame retardant, filler, and the other additives.

Examples of the organic metal salt-based flame retardant include ferrocene, acetylacetonate metal complexes, organic metal carbonyl compounds, organic cobalt salt compounds, organic sulfonic acid metal salts, compounds each having an ionic bond or coordinate bond between a metal atom and an aromatic compound or heterocyclic compound, and the like.

The amount of the organic metal salt-based flame retardant mixed is appropriately selected according to the type of the organic metal salt-based flame retardant, the other components of the curable resin composition, and the desired degree of flame retardancy. For example, the organic metal salt-based flame retardant is preferably mixed in a range of 0.005 to 10 parts by mass in 100 parts by mass of the curable resin composition containing all of the epoxy component, the curing agent, the non-halogen flame retardant, filler, and the other additives.

If required, an inorganic filler can be mixed in the curable resin composition of the present invention. Examples of the inorganic filler include fused silica, crystalline silica, alumina, silicon nitride, aluminum hydroxide, and the like. When the amount of the inorganic filler mixed is particularly increased, the fused silica is preferably used. Although either crushed or spherical fused silica can be used, the spherical fused silica is preferably mainly used for increasing the amount of the fused silica mixed and suppressing an increase in melt viscosity of a molding material. In order to further increase the amount of the spherical silica mixed, the grain size distribution of the spherical silica is preferably properly adjusted. The filling rate is preferably in the range of 0.5 to 100 parts by mass in 100 parts by mass of the curable resin composition. In the use for an application such as a conductive paste, conductive filler such as a silver powder, a copper powder, or the like can be used.

If required, various compounding agents such as a silane coupling agent, a mold release agent, a pigment, an emulsifier, etc. can be added to the curable composition of the present invention.

The curable composition of the present invention can be produced by uniformly mixing the above-described components. The curable composition of the present invention containing the epoxy component, the curing agent, and if required, further the curing accelerator can be easily formed into a cured product by the same as a general known method. Examples of the cured product include molded cured products such as a laminate, a cast product, an adhesive layer, a coating film, a film, and the like.

Applications using the curable composition of the present invention include printed circuit board materials, resin casting materials, adhesives, interlayer insulating materials for build-up substrates, adhesive films for build-up, and the like. Among these various applications, in the application to insulating materials for printed circuit boards and, electronic circuit boards and adhesive films for build-up, the resin composition can be used as an insulating material for so-called substrates for built-in electronic parts in which a passive part such as a capacitor and an active part such as a IC chip are embedded in a substrate. Among these, the resin composition is preferably used for printed circuit board materials and adhesive films for build-up in view of characteristics such as high heat resistance and flame retardancy.

When a printed circuit board is produced using the curable composition of the present invention, a method is given, in which a resin composition varnish is prepared by further mixing a varnish-like curable resin composition containing the organic solvent (C) with an organic solvent (C), a reinforcement substrate is impregnated with the resin composition varnish, and a copper foil is pressure-bonded thereon under heating. Examples of the reinforcement substrate which can be used include paper, a glass cloth, a glass nonwoven fabric, aramid paper, an aramid cloth, a glass mat, a glass roving cloth, and the like. In further detail, in the method, the varnish-like curable resin composition is heated at a heating temperature according to the type of solvent used, preferably 50 to 170° C., to form a prepreg as a cured product. The mass ratio between the resin composition and the reinforcement substrate used is not particularly limited but is preferably adjusted so that the resin content in the prepreg is 20 to 60% by mass. Next, the prepregs formed as described above are stacked by a usual method, and a copper foil is appropriately laminated thereon and heat-pressure bonded at 170 to 250° C. for 10 minutes to 3 hours under a pressure of 1 to 10 MPa, thereby producing the intended printed circuit board.

When the curable resin composition of the present invention is used as a resist ink, an example of a method is one in which a resist ink composition is prepared by adding a cationic polymerization catalyst as a catalyst for the curable resin composition and further a pigment, talc, and filler, applied on a printed board by a screen printing method, and then cured to form a resist ink cured product.

When the curable composition of the present invention is used as conductive paste, examples of a usable method include a method of preparing a composition for an anisotropic conductive film by dispersing conductive fine particles in the curable resin composition, and a method of preparing a circuit-connecting paste resin composition or an anisotropic conductive adhesive which is liquid at room temperature.

As a method for producing an interlayer insulating material for a build-up board from the curable composition of the present invention, for example, the curable resin composition appropriately containing rubber and filler is applied to a circuit board having a circuit formed thereon by a spray coating method, a curtain coating method, or the like, and then cured. Then, if required, predetermined through holes are formed, and then a surface is treated with a coarsening agent, washed with hot water to form projections and depressions, and then plated with a metal such as copper. As the plating method, electroless plating and electrolytic plating are preferred, and an oxidizer, an alkali, and an organic solvent can be used as the coarsening agent. Such an operation is successively repeated according to demand to alternately build up a resin insulating layer and a conductor layer of a predetermined circuit pattern, thereby producing a build-up board. However, the through holes are formed after the outermost resin insulating layer is formed. Also, a build-up substrate can be formed by pressure-bonding a copper foil with a resin, which is formed by semi-curing the resin composition on the copper foil, under heating at 170 to 250° C. on the circuit board having a circuit formed thereon, without the steps of forming a coarsened surface and of plating.

An example of a method for producing an adhesive film for build-up from the curable composition of the present invention is a method in which the curable composition of the present invention is applied onto a support film to form a resin composition layer, producing an adhesive film for a multilayer printed circuit board.

When the curable composition of the present invention is used for an adhesive film for build-up, it is important for the adhesive film to soften under a lamination temperature condition (usually 70° C. to 140° C.) in a vacuum lamination method and to exhibit fluidity (resin flow) which permits resin filling in via holes or through holes present in a circuit board at the same time as lamination on the circuit board. The above-described components are preferably mixed so as to exhibit these characteristics.

The through holes in a multilayer printed circuit board generally have a diameter of 0.1 to 0.5 mm and a depth of 0.1 to 1.2 mm, and preferably generally can be filled with a resin within this range. When both surfaces of the circuit board are laminated, the through holes are preferably about ½ filled.

Specifically, in the method for producing the adhesive film, the varnish-like curable resin composition of the present invention is prepared and then applied onto a surface of a support film (y), and further the organic solvent is dried by heating or hot-air spraying to form a layer (x) of the curable resin composition, producing the adhesive film.

The thickness of the layer (x) formed is not less than the thickness of the conductor layer. Since the thickness of the conductor layer provided in the circuit board is generally in the range of 5 to 70 μm, the thickness of the resin composition layer is preferably 10 to 100 μm.

The layer (x) according to the present invention may be protected by a protecting film described below. Protecting by the protecting film can prevent adhesion of dust to the surface of the resin composition layer and scratches thereon.

Examples of the support film and the protecting film include films of polyolefins such as polyethylene, polypropylene, polyvinyl chloride, and the like, polyesters such as polyethylene terephthalate (may be abbreviated as "PET" hereinafter), polyethylene naphthalate, and the like, polycarbonate, polyimide, release paper, and metal foils such as a copper foil, an aluminum foil, and the like. The support film and the protecting film may be subjected to MAD treatment, corona treatment, or release treatment.

The thickness of the support film is not particularly limited, but is generally 10 to 150 μm and preferably in a range of 25 to 50 μm. The thickness of the protecting film is preferably 1 to 40 μm.

The support film (y) is separated after being laminated on the circuit board or after the insulating film is formed by heat curing. When the support film (y) is separated after the adhesive film is heat-cured, adhesion of dust in the curing step can be prevented. When the support film is separated after curing, generally, the support film is previously subjected to release treatment.

Next, in the method for producing the multilayer printed circuit board using the adhesive film formed as described above, for example, when the layer (x) is protected by the protecting film, the protecting film is separated, and then the layer (x) is laminated on one or both surfaces of the circuit board by, for example, a vacuum lamination method so that the layer is in direct contact with the circuit board. The lamination method may be a batch mode or a continuous mode using a roll. In addition, if required, the adhesive film and the circuit board may be heated (preheated) before the lamination.

The lamination is preferably performed under the lamination conditions including a pressure-bonding temperature (lamination temperature) of 70° C. to 140° C. and a pressure-bonding pressure of 1 to 11 kgf/cm$^2$ (9.8×10$^4$ to 107.9×10$^4$ N/m$^2$), and under reduced air pressure of 20 mmHg (26.7 hPa) or less.

As a method for producing a cured product of the present invention, the composition prepared by the above-described method may be heated in the temperature range of about 20° C. to about 250° C.

EXAMPLES

Next, the present invention is described in further detail with reference to examples and comparative examples, and "parts" and "%" below are on a mass basis unless otherwise specified. In addition, a softening point, $^{13}$C-NMR, and MS were measured under conditions described below.

1) GPC: The measurement conditions are as follows.
Measurement apparatus: "HLC-8220 GPC" manufactured by Tosoh Corporation
Column: Guard Column "HXL-L" manufactured by Tosoh Corporation
+"TSK-GEL G2000HXL" manufactured by Tosoh Corporation
+"TSK-GEL G2000HXL" manufactured by Tosoh Corporation
+"TSK-GEL G3000HXL" manufactured by Tosoh Corporation
+"TSK-GEL G4000HXL" manufactured by Tosoh Corporation
Detector: RI (differential refractometer)
Data processing: "GPC-8020 model II version 4.10" manufactured by Tosoh Corporation
Measurement Conditions:
Column temperature 40° C.
Developing solvent tetrahydrofuran
Flow rate 1.0 ml/min
Standard: using monodisperse polystyrene described below having a known molecular weight according to a measurement manual of the "GPC-8020 model II version 4.10".
(Polystyrene Used)
"A-500" manufactured by Tosoh Corporation
"A-1000" manufactured by Tosoh Corporation
"A-2500" manufactured by Tosoh Corporation
"A-5000" manufactured by Tosoh Corporation
"F-1" manufactured by Tosoh Corporation
"F-2" manufactured by Tosoh Corporation
"F-4" manufactured by Tosoh Corporation
"F-10" manufactured by Tosoh Corporation
"F-20" manufactured by Tosoh Corporation
"F-40" manufactured by Tosoh Corporation
"F-80" manufactured by Tosoh Corporation
"F-128" manufactured by Tosoh Corporation
Sample: prepared by filtering, with a microfilter, a tetrahydrofuran solution of 1.0% by mass in terms of resin solid content (50 μl).
3) $^{13}$C-NMR: The measurement conditions are as follows.
Apparatus: AL-400 manufactured by JEOL, Ltd.
Measurement mode: SGNNE (NOE-suppressed 1H complete decoupling method)
Solvent: dimethylsulfoxide
Pulse angle: 45° C. pulse
Sample concentration: 30 wt %
Number of acquisitions: 10000
4) MS: double focusing mass spectrometer AX505H (FD505H) manufactured by JEOL, Ltd.

Example 1

Figure 2:
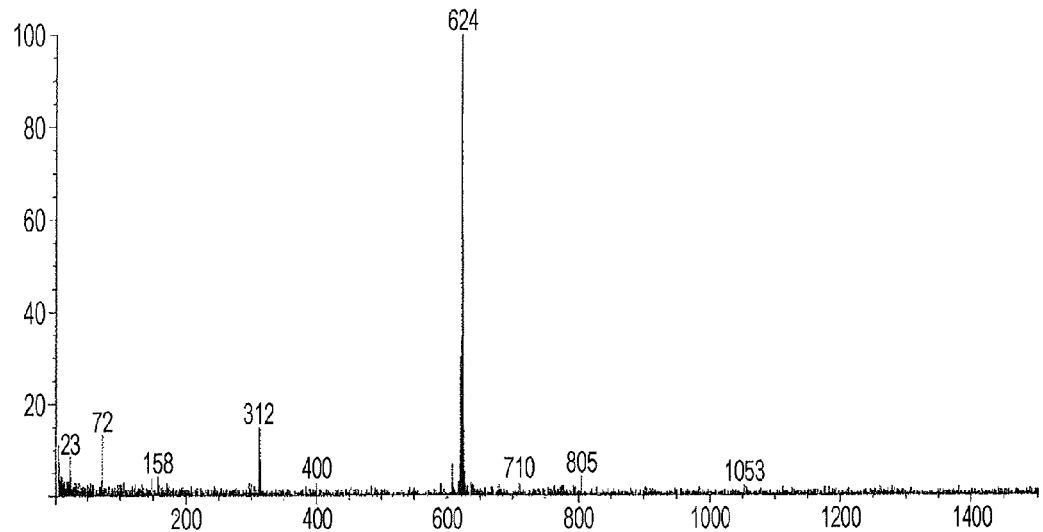
FIG. 2 is a MS spectrum of naphthol compound (A-1) produced in Example 1.

In a flask provided with a thermometer, a dropping funnel, a cooling tube, a fractionating column, and a stirrer, 216 parts by mass (1.50 moles) of α-naphthol, 146 parts by mass (1.80 moles) of a 37 mass % aqueous formaldehyde solution, 121 parts by mass of isopropyl alcohol, and 46 parts by mass (0.56 moles) of a 49% aqueous sodium hydroxide solution were charged and stirred at room temperature under nitrogen blowing. Then, the resultant mixture was heated to 80° C. and stirred for 1 hour. After the completion of reaction, the mixture was neutralized by adding 40 parts by mass of sodium dihydrogen phosphate and then cooled, and resultant crystals were filtered off. The crystals were repeatedly washed three times with 200 parts by mass of water and then dried by heating under reduced pressure to produce 224 parts by mass of naphthol compound (A-1). The resulting naphthol compound (A-1) had a hydroxyl equivalent of 156 g/eq. FIG. 1 shows a GPC chart of the naphthol compound, and FIG. 2 shows a MS spectrum thereof.

Figure 3:
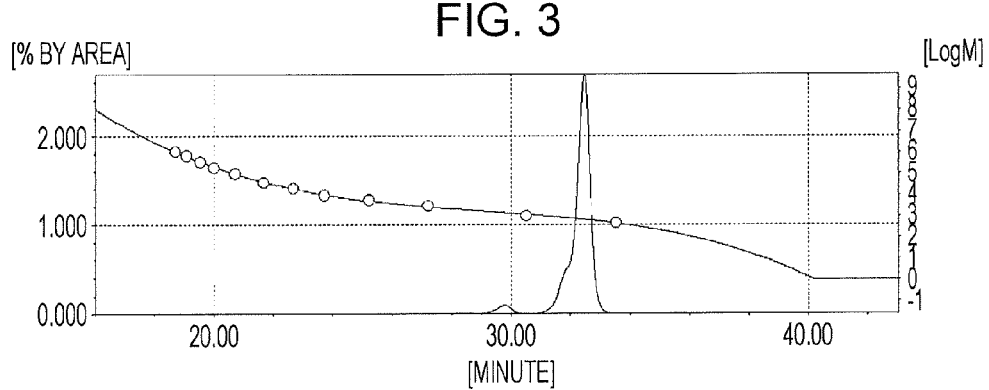
FIG. 3 is a GPC chart of epoxy compound (A-2) produced in Example 1.
Figure 4:
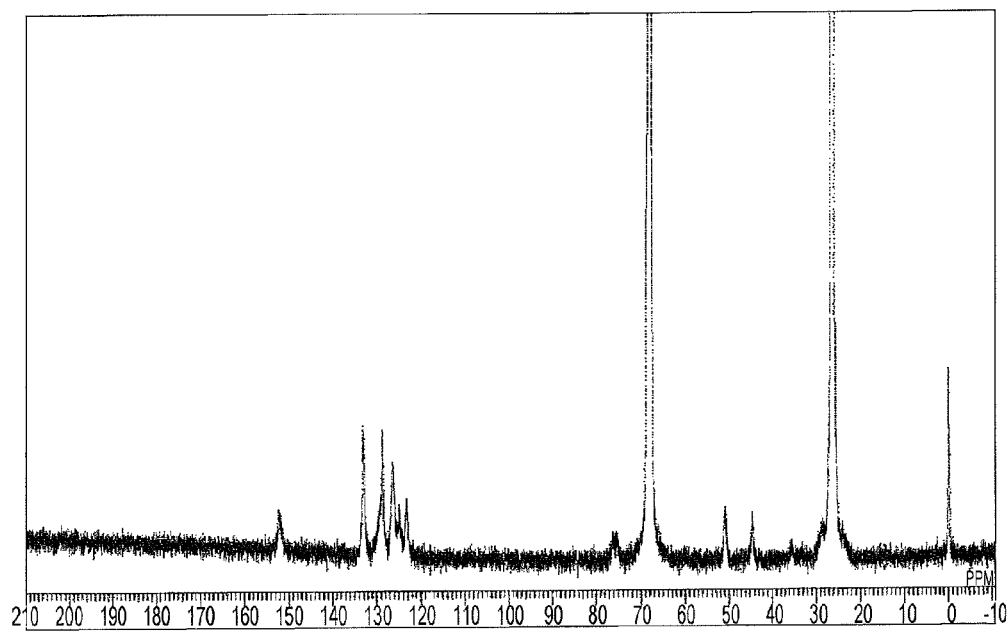
FIG. 4 is a $^{13}$C-NMR chart of epoxy compound (A-2) produced in Example 1.
Figure 5:
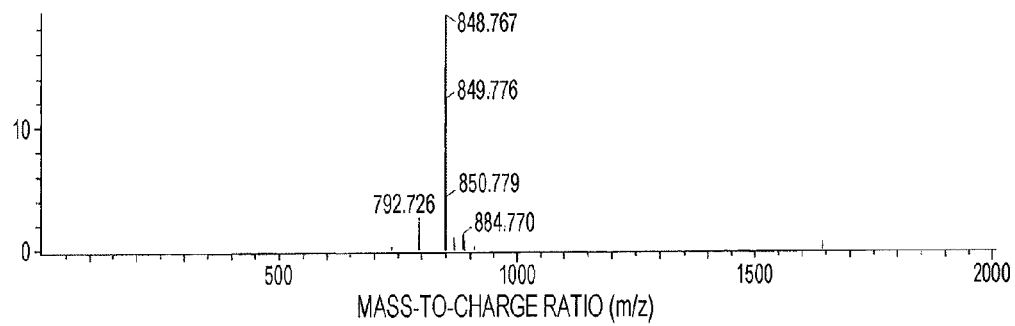
FIG. 5 is a MS spectrum of epoxy compound (A-2) produced in Example 1.
Figure 6:
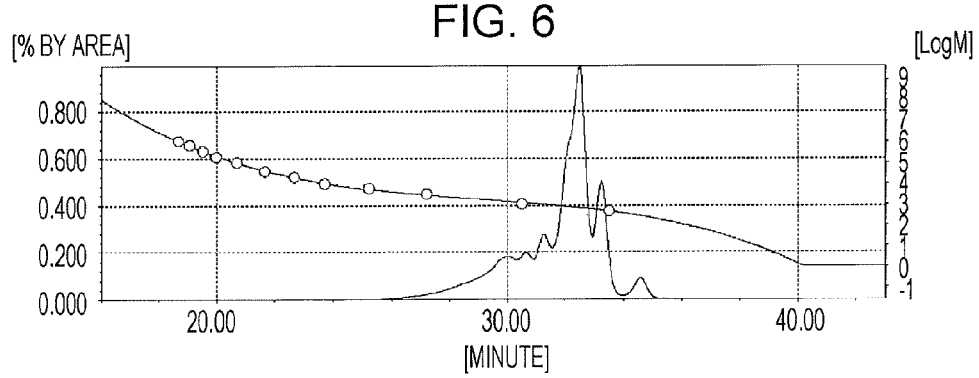
FIG. 6 is a GPC chart of epoxy resin mixture (A-3) produced in Example 2.

Next, in a flask provided with a thermometer, a cooling tube, and a stirrer, 156 parts by mass (hydroxyl group, 1.0 equivalent) of the phenol compound (A-1) produced by the above-described reaction, 463 parts by mass (5.0 moles) of epichlorohydrin, and 53 parts by mass of n-butanol were charged under nitrogen purge to prepare a solution. The resultant solution was heated to 50° C., and then 220 parts by mass (1.10 moles) of a 20% aqueous sodium hydroxide solution was added over 3 hours, followed by further reaction at 50° C. for 1 hour. After the completion of reaction, unreacted epichlorohydrin was distilled off at 150° C. under reduced pressure. Then, the resulting crude epoxy resin was dissolved by adding 300 parts by mass of methyl isobutyl ketone and 50 parts by mass of n-butanol. Further, 15 parts by mass of a 10 mass % aqueous sodium hydroxide solution was added to the solution, followed by reaction at 80° C. for 2 hours. Then, water washing was repeated three times with 100 parts by mass of water until the washing solution became neutral pH. Then, the reaction system was dehydrated by azeotropy and then subjected to microfiltration, and then the solvent was distilled off under reduced pressure to produce 201 parts by mass of intended epoxy compound (A-2). The resulting epoxy compound (A-2) had an epoxy equivalent of 239 g/eq. FIG. 3 shows a GPC chart of the epoxy compound (A-2), FIG. 4 shows a $^{13}$C-NMR chart, and FIG. 5 shows a MS spectrum. The content of a compound with n=4 in the structural formula 1 was 85.6% according to the GPC chart, and a peak of 848 showing n=4 was detected in the MS spectrum.

Example 2

Figure 7:
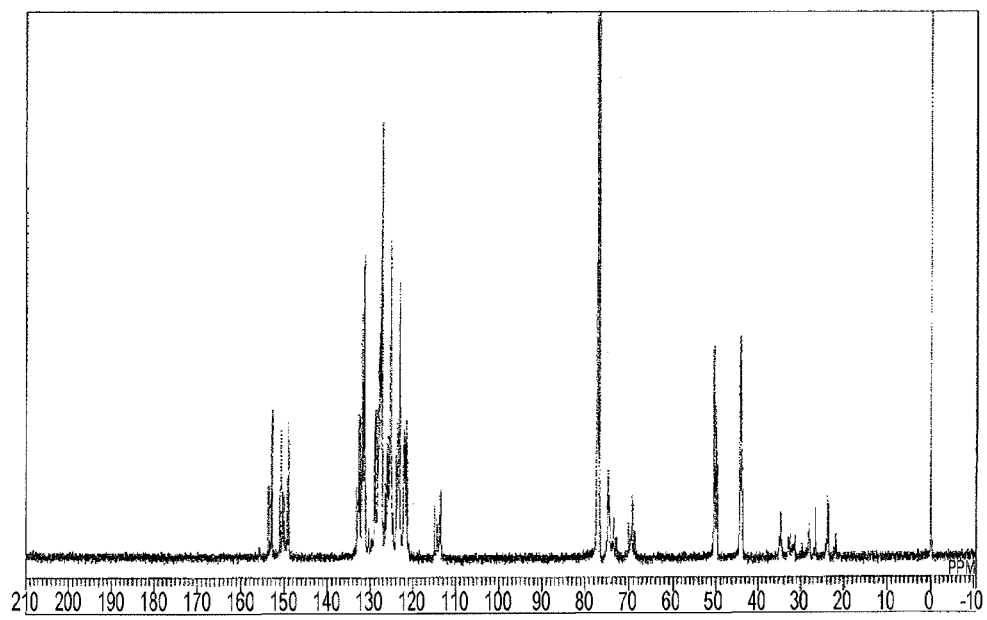
FIG. 7 is a $^{13}$C-NMR chart of epoxy resin mixture (A-3) produced in Example 2.
Figure 8:
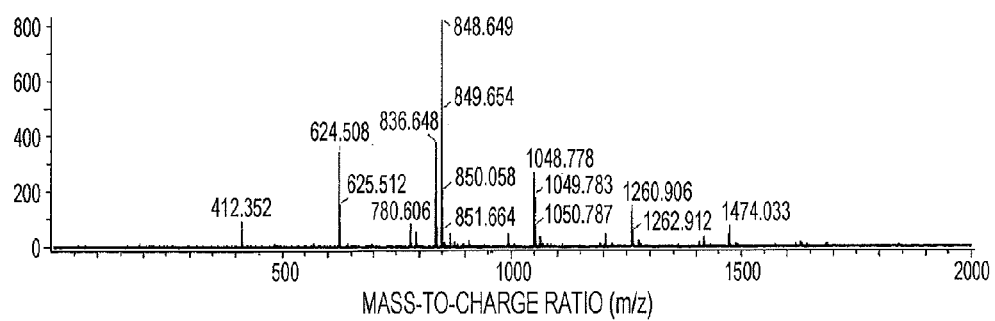
FIG. 8 is a MS spectrum of epoxy resin mixture (A-3) produced in Example 2.

According to the same method as in Example 1 except that 144 parts by mass (1.00 mole) of α-naphthol and 72 parts by mass (0.50 moles) of β-naphthol were used in place of 216 parts by mass (1.50 moles) of α-naphthol, 199 parts of mass of epoxy resin mixture (A-3) was prepared. The resultant epoxy resin mixture (A-3) had a softening point of 133° C. (B & R method), a melt viscosity of 115.0 dPa·s (measurement method: ICI viscometer method, measurement temperature: 150° C.), and an epoxy equivalent of 240 g/eq. FIG. 7 shows a GPC chart of the epoxy resin mixture (A-3), FIG. 7 shows a $^{13}$C-NMR chart, and FIG. 8 shows a MS spectrum. A peak of 848 showing n=4 in the structural formula 1 was detected in the MS spectrum, and the content of a compound with n=4 in the structural formula 1 was 34.1% according to the GPC chart. Therefore, it was found that the epoxy resin mixture (A-3) is a mixture of an epoxy compound with n=4 in the structural formula 1 and polyglycidyl ether of α-naphthol/(β-naphthol co-condensed novolac.

Example 3

Figure 9:
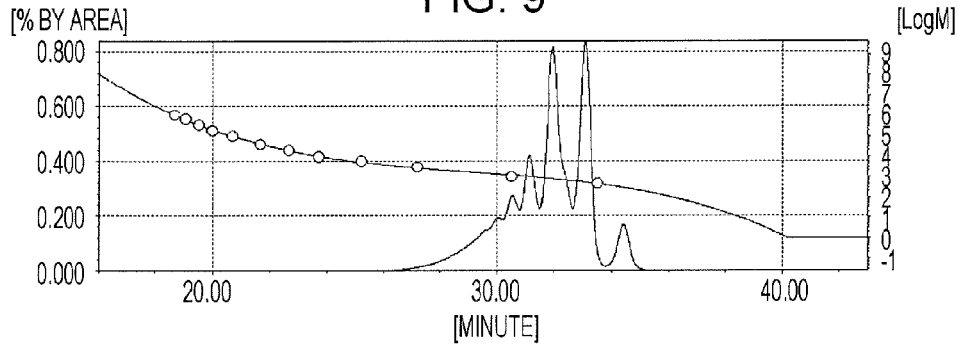
FIG. 9 is a GPC chart of epoxy resin mixture (A-4) produced in Example 3.

According to the same method as in Example 1 except that 108 parts by mass (0.75 moles) of α-naphthol and 108 parts by mass (0.75 moles) of β-naphthol were used in place of 216 parts by mass (1.50 moles) of α-naphthol, 200 parts of mass of epoxy resin mixture (A-4) was prepared. The resultant epoxy resin mixture (A-4) had a softening point of 114° C. (B & R method), a melt viscosity of 80.0 dPa·s (measurement method: ICI viscometer method, measurement temperature: 150° C.), and an epoxy equivalent of 236 g/eq. FIG. 9 shows a GPC chart of the epoxy resin mixture (A-4). The content of a compound with n=4 in the structural formula 1 was 6.9% according to the GPC chart.

Comparative Example 1

In a flask provided with a thermometer, a dropping funnel, a cooling tube, a fractionating column, and a stirrer, 505 parts by mass (3.50 moles) of α-naphthol, 158 parts by mass of water, and 5 parts by mass of boric acid were charged and stirred while being heated from room temperature to 100° C. over 45 minutes. Then, 177 parts by mass (2.45 moles) of a 42 mass % aqueous formalin solution was added dropwise to the mixture over 1 hour. After the completion of addition, the mixture was further stirred at 100° C. for 1 hour and then heated to 180° C. over 3 hours. After the completion of reaction, water remaining in the reaction system was removed by heating under reduced pressure to produce 498 parts by mass of naphthol resin (A-5). The resulting naphthol resin (A-5) had a softening point of 133° C. (B & R method) and a hydroxyl equivalent of 154 g/eq. In addition, a calixarene structure could not be confirmed by the results of the MS spectrum.

Next, 154 parts by mass (hydroxyl group 1.0 equivalent) of the naphthol resin (A-5) was reacted with epichlorohydrin by the same method as in Example 1 to produce 193 parts by mass of epoxy resin (A-6). The epoxy equivalent was 236 g/eq.

Examples 4 to 6 and Comparative Example 2

(A-2), (A-3), (A-4), or (A-6) as an epoxy component, TD-2131 (phenol novolac phenol resin, hydroxyl equivalent: 104 g/eq) manufactured by DIC Corporation as a phenol resin, and triphenylphosphine (TPP) as a curing accelerator were mixed to have each of the compositions shown in Table 1, molded with a press at a temperature of 150° C. for 10 minutes, and then post-cured at a temperature of 175° C. for 5 hours to form cured products. For the physical properties of each of the cured products, an evaluation sample was formed by the method below using each of the compositions and measured with respect to heat resistance and a coefficient of thermal expansion by the methods described below. The results are shown in Table 1.

<Heat Resistance <Glass Transition Temperature)>

A temperature at which a change in elastic modulus was maximized (highest rate of change in tan δ) was measured as a glass transition temperature using a viscoelasticity measuring device (DMA: solid viscoelasticity measuring device "RSA II" manufactured by Rheometrics Co., rectangular tension method; frequency 1 Hz, heating rate 3° C./min).

<Coefficient of Thermal Expansion>

Compression-mode thermal mechanical analysis was performed using a thermal mechanical analyzer (TMA: "SS-6100" measured by Seiko Instruments Co., Ltd.). At the second measurement (measurement load: 88.8 mN, heating rate: 3° C./min (two times), measurement temperature range: −50° C. to 300° C.), a coefficient of linear expansion (average expansion coefficient in a temperature range of 40° C. to 60° C.) was measured.

TABLE 1

|  |  | Example 4 | Example 5 | Example 6 | Comparative Example 1 |
|---|---|---|---|---|---|
| Epoxy resin | A-2 | 69.7 |  |  |  |
|  | A-3 |  | 69.8 |  |  |
|  | A-4 |  |  | 69.4 |  |
|  | A-6 |  |  |  | 69.4 |
| Curing agent | TD-2131 | 30.3 | 30.2 | 30.6 | 30.6 |
| TPP |  | 1.0 | 1.0 | 1.0 | 1.0 |
| Heat resistance (° C.) |  | 245 | 231 | 218 | 206 |
| Coefficient of thermal expansion (ppm) |  | 30 | 33 | 41 | 51 |

TD-2131: phenol novolac resin ("TD-2131" manufactured by DIC Corporation, hydroxyl equivalent 104 g/eq)
TPP: triphenylphosphine

The invention claimed is:

1. An epoxy compound having a resin structure represented by the following structural formula 1:

[Chem. 1]

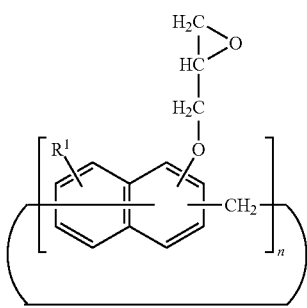

(in the formula, R¹s each independently represent a hydrogen atom, an alkyl group, or an alkoxy group, and n is a repeat unit and 2, 4, 6, or 8).

2. A curable resin composition comprising an epoxy compound (A) and a curing agent (B) as essential components, wherein the epoxy compound according to claim 1 is used as the epoxy compound (A).

3. The curable composition according to claim 2, wherein in addition to the epoxy compound (A) and the curing agent (B), a naphthalene-based epoxy resin (A') other than the epoxy compound (A) is used.

4. The curable resin composition according to claim 3, wherein the ratio between the epoxy compound (A) and the naphthol novolac epoxy resin (A') present is such that the content ratio of the naphthalene-based epoxy resin (A') other than the epoxy compound (A) is 3 to 50% in terms of area ratio in GPC measurement of a mixture of both.

5. A cured product produced by a curing reaction of the curable composition according to claim 2.

6. A cured product produced by a curing reaction of the curable composition according to claim 3.

7. A cured product produced by a curing reaction of the curable composition according to claim 4.

* * * * *